United States Patent
Wilson et al.

(12)

(10) Patent No.: US 6,310,186 B1
(45) Date of Patent: Oct. 30, 2001

(54) PURIFICATION OF BIOLOGICAL PREPARATIONS

(76) Inventors: Mark Jonathon Wilson, 31 Broad Lane, Cottenham, Cambridge, CB4 8SW; Michael Denis Johnston, 9 The Crescent, Impington, Cambridge CB4 9NY; Deirdre Anne Glenn, 22 The Oaks, Milton, Cambridge, CB4 6ZG; Sean Patrick Gallagher, 38 Long Reach Road, Chesterton, Cambridge, CB4 1UH, all of (GB)

( * ) Notice: Subject to any disclaimer, the term of this patent is extended or adjusted under 35 U.S.C. 154(b) by 0 days.

(21) Appl. No.: 09/541,815

(22) Filed: Apr. 3, 2000

(30) Foreign Application Priority Data

Apr. 1, 1999 (GB) .................................................. 9907553

(51) Int. Cl.[7] ...................................................... C07K 1/20
(52) U.S. Cl. .......................... 530/412; 530/415; 530/417; 530/351; 530/371; 536/25.4; 536/23.1; 536/123.1; 210/198.2; 210/651
(58) Field of Search ..................................... 530/351, 371, 530/412, 415, 417; 536/123.1, 23.1; 210/198.2, 651

(56) References Cited

U.S. PATENT DOCUMENTS 4,707,542 * 11/1987 Friedman et al. .................... 530/371
4,894,439 * 1/1990 Dorin et al. ......................... 530/351

OTHER PUBLICATIONS

Below, B., Zhou, Y., Wang, S., Nystrom, L.–E., Janson, J.–C. Journal of Chromatography A 679, 67–83 (1994). Purification of recombinant human granulocyte–macrophage colony–stimulating factor from the inclusion bodies produced by transformed *E. coli* cells.*

* cited by examiner

*Primary Examiner*—Christopher S. F. Low
*Assistant Examiner*—Chih-Min Kam
(74) *Attorney, Agent, or Firm*—Klarquist Sparkman, LLP

(57) ABSTRACT

This invention relates to the purification of biological preparations such as proteins and nucleic acids, especially for example proteins that have been produced by recombinant DNA techniques in bacteria. In a particular embodiment, the invention concerns improved methods for reducing the content of contaminants in biological preparations, e.g. recombinant proteins produced in host bacteria.

13 Claims, No Drawings

PURIFICATION OF BIOLOGICAL PREPARATIONS

PRIORITY DATA

This application claims the benefit of foreign priority under 35 U.S.C. §119(a)–(d) from Great Britain Application No. 990753.3, filed Apr. 1, 1999, herein incorporated by reference.

This invention relates to the purification of biological preparations such as proteins and nucleic acids, especially for example proteins that have been produced by recombinant DNA techniques in bacteria. In a particular embodiment, the invention concerns improved methods for reducing the content of contaminants in biological preparations, e.g. recombinant proteins produced in host bacteria.

BACKGROUND OF THE INVENTION AND PRIOR ART

It is known to produce recombinant proteins in gram negative host bacteria, for example *E.coli,* Pseudomonas, Vibrio spp. and *Methylophilus methylotrophus.*

One difficulty that can be encountered in this approach is that *E.coli,* and other such gram negative host bacteria useful for the expression of heterologous proteins are able to produce bacterial toxins such as endotoxins, which are integral lipo-polysaccharide (LPS) components of the bacterial cell wall, and which can be highly pyrogenic and can cause febrile reactions in animals.

It is desirable to reduce contaminating endotoxins in biological preparations when they are encountered.

There are known bioassays to detect bacterial endotoxin contamination of biological materials: the test used is the Chromagenic peptide endpoint method and this test has been adopted by the European Pharmacopoeia Commission and is described in 1999 European Pharmacopoeia—Supplement 1999, and can be used when needed for the purposes of the present invention.

Certain methods intended to remove or reduce levels of contaminating endotoxin from biological materials e.g. proteins are already known in the art.

Anion exchange chromatography for endotoxin removal is discussed by K. Khandake in an article entitled "Effective Removal of Negatively Charged Interfering Moleculed from Proteins" (U.S. Bulletin 2204, a technical bulletin from BioRad lnc., N.J., U.S.A.). Such chromatography is also discussed in "Why Anion Exchange Works So Well for Endotoxin Removal . . . Sometimes", (P. Gagnon, in Summer 1998 issue of "Validated Biosystems Quarterly Resource Guide for Downstream Processing, Validated Biosystems Inc., Tucson, Ariz., U.S.A.) K. C. Hou and R. Zaniewski, in Biotechnology and Applied Biochemistry 12, 315–324, 1990, describe endotoxin separation from albumin and gamma-globulin solutions using anion-exchange polymeric matrices carrying DEAE or QAE functional groups.

T. E. Karplus et al., in Journal of Immunological methods, 105, 211–220, 1987, describe the use of affinity-binding using polymyxin B-Sepharose (TM) in a method for reducing endotoxin contamination in catalase and IgG solutions.

K. W. Talmadge and C. J. Siebert, in Journal of Chromatography, 476, 175–185, 1989, report separation of endotoxin from serum albumin and IgG using a polymyxin-derivatised macroporous polymer affinity column.

F. B. Anspach and O. Hilbeck, in Journal of Chromatography A, 711, 81–92, 1995, describe the use of histidine, histamine and polymyxin B affinity sorbents in separation of *E. coli*-derived endotoxin from serum albumin and lysozyme. The authors concluded that "an endotoxin-specific sorbent for general decontamination of protein solutions seems not to be available".

The present inventors consider that endotoxin removal from biological materials remains a problem and that there remains a need for further techniques for endotoxin removal. Accordingly, an aim of the present invention is to provide new purification procedures for the reduction of endotoxin contamination e.g. associated with recombinant nucleic acids, or with recombinant proteins, for example proteins produced in host bacteria.

SUMMARY AND DESCRIPTION OF THE INVENTION

According to an aspect of the invention we provide a method for separating bacterial endotoxin associated as a contaminant with biological material which comprises, preferentially adsorbing the endotoxin onto a solid phase by contacting the biological material with a hydrophobic solid phase in the presence of a charged solubilising agent and a water soluble salt.

This process is particularly applicable under conditions where the biological material to be decontaminated is less hydrophobic than the endotoxin, and this can be assessed, e.g. as described below.

To determine whether endotoxin is less hydrophobic than the biological material under test, the unbound material obtained from contacting the biological material with the solid phase, can be tested for either the presence of endotoxin, or it can be tested for the presence of the biological material. Alternatively, the unbound material can be tested to determine levels of both endotoxin and biological material. When the unbound material from the test is found to contain substantially more of the wanted biological material than of the endotoxin this indicates that the wanted biological material is less hydrophobic than the endotoxin, and vice versa.

For the purpose of carrying out such testing, bacterial endotoxin contamination of biological material, e.g. protein can be determined using the Chromagenic peptide endpoint method described in 1999 European Pharmacopoeia—Supplement 1999. When the biological material is a protein or a peptide it can be detected for example, by Western blotting of an eluate sample. When the biological material is DNA it can be detected for example, by Southern blotting of an eluate sample. When the biological material is RNA it can be detected for example, by Northern blotting of an eluate sample.

The biological material which it can be desired to separate from associated endotoxin can be for example, a protein or a peptide susceptible to endotoxin contamination. For example, certain proteins may be found to be contaminated to unacceptable levels by endotoxin when expressed in the form of inclusion bodies in an *E.coli* heterologous expression system, and when the inclusion bodies are solubilised in standard salt or urea solutions.

Thus, examples of the process according to the invention can be used in the purification of protein or peptide susceptible to endotoxin contamination, e.g. because they can bind with endotoxin.

Certain examples of the process can be used for purification of recombinant proteins, for example a viral subunit antigen for vaccine use. The viral antigen can be for example, an antigen of papillomavirus, e.g. L2, E6 or E7, or a fusion protein involving one or more of these antigens e.g. as described in WO 96/26277 (Cantab Pharmaceuticals Research Limited, Whittle et al.).

Otherwise, the biological material which it is desirable to separate from endotoxin can be for example, a nucleic acid susceptible to endotoxin contamination. The nucleic acid can be DNA or RNA for use, e.g. as a vaccine, or for gene therapy.

The endotoxin which it is desirable to separate from associated biological material can be for example, lipopolysaccharide from gram negative bacteria, e.g. E.coli.

The hydrophobic solid phase can be for example a derivatised particulate material with a particle or bead size suitable for use as a column chromatography matrix, or alternatively it can be a derivatised sheet material, e.g. in the form of a membrane.

The hydrophobic particulate or sheet material can be a hydrophilic base material that has been derivatised with hydrophobic groups.

The hydrophilic base material can be, for example, a polysaccharide, e.g. agarose or dextran, or alternatively it can be, for example, a polyamide, e.g. acrylamide. Alternatively, the hydrophobic matrix can be either a non-derivatised or derivatised hydrophobic base matrix, for example, a polystyrene di-vinyl benzene co-polymer base matrix, e.g. Source (TM) matrix, available from Pharmacia, or Poros (TM) available from PerSeptive Biosystems.

The hydrophobic groups used to derivatise the base matrix can be for example aromatic groups, e.g. phenyl groups, e.g. as in Phenyl Sepharose (TM) (Pharmacia). Alternatively, the hydrophobic derivatives can be alkyl groups, e.g. alkyl groups of 2 to 18 carbon atoms, e.g. alkyl groups of 4 to 8 carbon atoms.

A suitable and presently preferred hydrophobic solid phase can comprise Phenyl-Sepharose (TM) gel, which is a macroporous cross linked agarose gel in a bead form derivatised with phenyl groups, available from Pharmacia.

The charged solubilising agent used in the process of the invention can be, for example, a positively charged agent, e.g. guanidinium ion, e.g in the form of guanidine hydrochloride, or alternatively it can be a negatively charged agent, e.g. thiocyanate, e.g. in the form of sodium thiocyanate.

Alternatively, the charged solubilising agent can be a charged detergent such as a positively charged detergent, e.g. cetyl-trimethyl ammonium ion, supplied as e.g. cetyl-trimethyl ammonium chloride (CTAC), or it can be a negatively charged detergent, e.g. dodecyl sulphate in the form of sodium dodecyl sulphate (SDS).

The charged solubilising agent is used at a concentration that can facilitate separation of the biological substance and endotoxin and that is soluble in the presence of the salt used. Preferably, the charged solubilising agent is used at a high concentration. For example, when the solubilising agent is guanidine hydrochloride, the concentration of the solubilising agent can be in the range from 2 to 8.5M, and preferably at least 4M, e.g. in the range at least 4 to 6 or 7 or 8M.

Suitable water-soluble salts include those salts which are usually used to precipitate biological material by a salting out effect. Examples of suitable salts that can be used include ammonium sulphate, sodium sulphate and sodium chloride. In the present context it is considered that they are acting as lyotropic substances.

Preferably, the concentration of salt used is the highest concentration in which the biological material and associated endotoxin remain soluble in the presence of the solubilising agent. When the salt used is ammonium sulphate the concentration can be in the range from 0.1M to about 4.0M, and preferably at least 0.5M, e.g. in the range 0.5 to 0.75 or 1.0M. When the salt used is sodium chloride the concentration can be in the range from 0.5M to about 5.0M, and preferably at least 2.0M, e.g. in the range 2.0 to 3.0 to 4.0M.

It has for example been found that where a fusion protein comprising sequences of human papillomavirus proteins, e.g. substantially full-length HPV L2 fused with E6 and/or E7, is found to be contaminated with bacterial endotoxin, the protein can be separated from the endotoxin in the eluate of a phenyl-sepharose (TM) column using a mobile aqueous phase comprising buffered high-molar guanidine hydrochloride denaturant and salt, e.g. ammonium sulphate, with the endotoxin substantially binding to the column, and the eluted fusion protein product can for example have been freed from endotoxin to the extent of a reduction of endotoxin contamination levels up to 100 fold or more, e.g. up to 500-fold or more, e.g. up to about 1000-fold, such that levels of endotoxin associated with the fusion protein product are below about 1500 EU/mg, e.g. less than 1000 EU/mg, e.g. less than 500 EU/mg, e.g. less than 250 EU/mg, e.g. less than 100 EU/mg, e.g. less than 50 EU/mg.

The endotoxin reference standard referred to in the designation 'EU' is the U.S. Pharmacopoeia Endotoxin Reference Standard which has a defined potency of 10,000 USP Endotoxin Units (EU) and is described in 1999 European Pharmacopoeia—Supplement 1999. There is approximately 0.1 ng of endotoxin per EU.

In order to obtain further reduction of contaminants associated with the wanted biological material, for example endotoxin, DNA, or host cell contaminants, it can also be useful to carry out other purification steps on the wanted material in addition to the hydrophobic solid separation process already described.

For example, the partially purified product of the hydrophobic separation process can if desired be further purified by using chromatography. For example, an additional stage of hydrophobic interaction chromatography, or cation exchange chromatography, or anion exchange chromatography can be used to achieve further purification. Alternatively, gel filtration can be used for further purification e.g. using beads of cross-linked dextran gel such as Sephadex. Filtration techniques, for example membrane filtration, can also be used for further purification.

In a preferred example of a process according to the invention it has for example been found that the levels of contaminating endotoxin associated with the fusion protein comprising sequences of human papillomavirus proteins can be satisfactorily reduced by first carrying out the hydrophobic separation process as described above, and then by further treatment of the protein by anion exchange chromatography, e.g. using a Macroprep High Q (TM) column (BioRad Inc.), which comprises a hydrophilic macroporous methacrylate co-polymer base matrix derivatised with quarternary ammonium groups. The endotoxin and the protein bind to the column, and the protein is eluted in buffer comprising salt, whilst the endotoxin remains bound.

Preferably the salt concentration used for elution is a higher salt concentration than that used in the adsorption stage, e.g. containing 10% higher salt concentration or more, e.g. up to 20%, or more, e.g. up to about 50% higher salt concentration. Examples of suitable salts include ammonium sulphate and sodium chloride, e.g. 0.6M sodium chloride.

In certain examples of the invention, levels of contaminating endotoxin associated with the protein product have been reduced down to for example about 250 EU/mg, or less.

It can also be useful to concentrate the substantially purified biological product produced by the process according to the invention, by for example filtration, e.g. by membrane filtration.

According to a further aspect of the invention, there is provided a method for separating endotoxin and biological material, which comprises preferentially adsorbing the biological material onto a solid phase by contacting the biological material and endotoxin with a hydrophobic solid phase in the presence of a charged solubilising agent and a water soluble salt.

A process according to this aspect of the invention is particularly applicable under conditions where the biological material to be decontaminated is more hydrophobic than the endotoxin. This can be assessed using the test methods already described above.

When the more-hydrophobic biological material is adsorbed onto the solid phase it can be recovered for example by elution from the solid phase by a buffer comprising a lower salt concentration than that used in the adsorption stage, e.g. containing less than 90% of the salt concentration of the buffer used in the adsorption stage, e.g. less than 70%, e.g. less than 50%, e.g. less than 25%, The salt can be for example ammonium sulphate or sodium chloride.

Separation of endotoxin from the biological material can be determined as mentioned previously.

Proteins which have been substantially separated from endotoxin by processes according to the invention, whether used alone, or in combination with other purification steps, can be used for example as vaccine preparations, e.g. for therapeutic or for prophylactic use. For such uses they can be suitably formulated, for example with adjuvant, e.g. alum, or with other adjuvants such as Novosomes (TM) or other adjuvants mentioned in, for example, WO 96/26277 (Cantab Pharmaceuticals, Whittle et al.). Alternatively, the vaccine preparations can be administered without adjuvant.

Nucleic acids, for example DNA, which have been substantially separated from endotoxin by hydrophobic separation according to the invention, whether used alone, or in combination with other purification steps, can be used for example as vaccine preparations, or for gene therapy.

Biological materials which have been purified according to the invention, e.g. by the particular steps described in the example given below, can contain usefully reduced levels of endotoxin containing, either relative to the starting material, e.g. up to 100-fold or greater reduction, e.g. up to 500-fold or greater reduction, e.g. up to 1000-fold or greater reduction, e.g. up to 5000-fold or greater reduction, e.g. up to about 10,000-fold reduction; or in absolute terms containing, e.g. below about 1500 EU/mg, e.g. down to about 1000 EU/mg or less, e.g. down to about 500 EU/mg or less, e.g. down to about 250 EU/mg or less, e.g. down to about 150 EU/mg or less, e.g. down to about 100 EU/mg or less, e.g. down to about 50 EU/mg.

A preferred example of the invention is also described below without intent to limit the scope of the invention.

EXAMPLE

This example concerns preparation of a recombinant fusion protein incorporating in its sequence heterologous DNA encoding proteins L2, E7 and E6 of human papillomavirus type 16. The fusion protein is made in an *E. coli* host expression system using a method corresponding to that described in WO 96/26277 (Cantab Pharmaceuticals Research Limited, Whittle et al.). The fusion protein is produced by the *E.coli* host cells as inclusion bodies. If the protein is not to be purified immediately, then the host cell culture can be stored at −40 deg C., and it can then be thawed at 37 deg C. prior to use.

The protein can be prepared for purification as follows:

The starting material, which is the recombinant *E. coli* cell culture produced as described earlier, is homogenised in 50 mM Tris buffer (pH 8.0) containing 5 mM EDTA in order to produce a blended cell suspension. The *E.coli* cells are then disrupted by passage through a pressure homogeniser at 12,000 psi, to release the inclusion bodies. These inclusion bodies are then isolated as a pellet by centrifugation at 13000 g for 60 min. The isolated protein pellet obtained is then prepared for washing by centrifugation by resuspension in buffer containing 50 mM Tris (pH8.0), 10 mM EDTA, 1000 mM NaCl and 1% v/v Triton X-100. The suspension is then centrifuged at 13000 g for 30 min, and the pellet retained. This pellet is then resuspended in 2 mM Tris buffer (pH8.0), and is centrifuged at 13000 g for 60 min. The protein pellet is retained. If the isolated protein pellet is not to be used immediately it can be stored at −80 deg C.

The pellet is subsequently solubilised and denatured using a 6.0M guanidine hydrochloride buffer at pH7.0 which also contains 100 mM phosphate and 20 mM cysteine, 19 mls of buffer is added per gram of pellet. This is followed by centrifugation of the solubilised pellet at 13000 g for 60 min at 4 deg C. The supernatant obtained by centrifugation contains the solubilised fusion protein. If desired, the level of bacterial endotoxin contamination of the fusion protein can be determined by testing this supernatant. The test used can be that adopted by the European Pharmacopoeia Commission for this purpose, and described in 1999 European Pharmacopeia—Supplement 1999.

The protein can then be purified as follows:

The fusion protein sample is subject to a first stage hydrophobic interaction purification. The fusion protein sample taken for this stage is the supernatant obtained as mentioned above by centrifugation of the solubilised pellet. Sample preparation for this stage is done as follows; (a) 100 mM pH7.0 phosphate buffer containing 2.35M ammonium sulphate and 20 mM cysteine is added to the sample to a final concentration of 0.7M ammonium sulphate, in order to produce a high ammonium sulphate concentration, and (b) the sample is filtered using a 0.2 μm filter to remove residual particulate matter. The prepared sample is then loaded onto a Phenyl Sepharose (TM) hydrophobic interaction column. The column has previously been equilibrated with 100 mM phosphate buffer (pH7.0) containing 4.0M guanidine hydrochloride, 0.7M ammonium sulphate and 20 mM cysteine. Endotoxin from the sample binds to the column and protein flows through unbound or at least less strongly bound to endotoxin.

There then follows a second stage hydrophobic interaction purification. The fusion protein sample taken for this stage is the eluate obtained from the first stage hydrophobic affinity purification. Sample preparation for this stage is done as follows: (a) the protein is concentrated by filtration of the eluate through a 30 KDa membrane, (b) the concentrate produced is then diafiltered against at least 10 volumes of 100 mM phosphate buffer (pH7.0) containing, 8.0M urea, 100 mM ammonium sulphate and 20 mM cysteine, and (c)

ammonium sulphate solution containing 100 mM phosphate (pH7.0), 2.42M ammonium sulphate and 20 mM cysteine is added to the diafiltered concentrate to give a final concentration of 0.68M ammonium sulphate. This is to produce a high ammonium sulphate concentration in the sample. The prepared sample is then loaded onto a phenyl sepharose column. The column has previously been equilibrated with 50 mM Phosphate buffer (pH7.0) containing 8M urea, 0.68M ammonium sulphate and 20 mM cysteine. Protein binds to the column and protein-associated contaminants flow through unbound or at least less strongly bound. The protein is then ekyted using five volumes of elution buffer containing 50 mM phosphate (pH7.0), 8.0M urea, 0.15M ammonium sulphate and 20 mM cysteine. This protein-containing eluate is retained for the next stage. This protein-containing eluate is then further purified by cation exchange chromatography. The sample is prepared for this stage by gel filtration on a G25 superfine Sephadex (TM) column (Pharmacia) using a buffer containing 20 mM glycine (pH9.0), 8.0M urea and 20 mM cysteine in order to reduce the concentration of ammonium sulphate in the sample. The prepared sample is then loaded onto a CM fast flow Sepharose (TM) column (Pharmacia). The column has previously been equilibrated with buffer containing 20 mM glycine (pH9.0), 8.0M urea and 20 mM cysteine. The protein binds to the column and host cell contaminants flow through unbound or less strongly bound. The bound protein is then eluted using elution buffer containing 20 mM glycine (pH9.0), 8.0M urea, 0.6M sodium chloride and 20 mM cysteine. This eluate is retained for the next stage.

This protein eluate is then further purified by anion exchange chromatography. The sample is prepared for this stage by gel filtration on a G25 sephadex (TM) column using buffer containing 20 mM glycine (pH9.0), 8.0M urea, and 20 mM cysteine, this reduces the concentration of sodium chloride in the sample. The prepared sample is then loaded onto a Macroprep high Q (TM) anion exchange column (BioRad Inc.), and the column is incubated at room temperature for 12–20 hours. The column has previously been equilibrated with buffer containing 20 mM glycine (pH9.0), 8.0M urea, and 20 mM cysteine. The protein and contaminating endotoxin and DNA bind to the column, with the protein substantially less strongly bound. Following this, the bound protein is preferentially eluted using equilibration buffer which further comprises 0.6M sodium chloride. This eluate is retained for the next stage. The protein eluate obtained is concentrated by membrane filtration using a 30 Kda membrane. The amount of urea remaining in the concentrated protein eluate is then reduced by gel filtration of the eluate through a G25 sephadex column, using buffer containing 5 mM glycine (pH9.0) and 0.9 mM cysteine. The protein flows through the column. The protein eluate obtained is substantially free of contaminating endotoxin and other host cell contaminants. The protein sample can be stored at −40 deg C. or below, and can be prepared for storage by filtering it through a 0.2 μm filter to remove any contaminating micro-organisms. The filtrate obtained contains the protein, and can be stored in sterile containers.

The present disclosure extends to modifications and variations of the description given herein that will be apparent to the reader skilled in the art. The disclosure hereof, incorporating WO 96/26277 which is made an integral part hereof, is intended to extend in particular to classes and subclasses of the products and generally to combinations and sub-combinations of the features mentioned, described and referenced in the present disclosure. Without limiting the generality hereof, the invention extends in particular to the products of the techniques described and to their use as immunogens in pharmaceutical vaccine formulations. Documents cited herein are hereby incorporated in their entirety by reference for all purposes.

What is claimed is:

1. A method for separating bacterial endotoxin associated as a contaminant with biological material which comprises, (a) adsorbing endotoxin onto a solid phase by contacting the biological material and endotoxin with a hydrophobic solid phase in the presence of a charged solubilizing agent, which is about 2M to about 8.5M guanidine hydrochloride, and a water soluble salt, and then (b) eluting the non-adsorbed biological material from said solid phase, such that said endotoxin is separated from said biological material.

2. A method according to claim 1, in which the hydrophobic solid phase is a hydrophobic base matrix.

3. A method according to claim 1, in which the hydrophobic solid phase is a particulate material.

4. A method according to claim 3, in which the particulate material is a hydrophilic base material with exposed hydrophobic groups.

5. A method according to claim 1, in which the guanidine hydrochloride concentration is about 4M to about 8M.

6. A method according to claim 1, in which the water soluble salt is selected from the group consisting of ammonium sulfate, sodium sulfate and sodium chloride.

7. A method according to claim 5, in which the guanidine hydrochloride concentration is about 4M to about 6M.

8. A method according to claim 1, wherein the guanidine hydrochloride concentration is about 4M and the water soluble salt is about 0.5 M to about 0.75M ammonium sulfate.

9. A method according to claim 3, wherein the hydrophobic solid phase is a column chromatography matrix.

10. A method according to claim 4, wherein the hydrophilic base material is a macroporous cross-linked agarose gel with hydrophobic phenyl groups.

11. A method according to claim 1, wherein the biological material is a protein produced in the form of inclusion bodies in an *Escherichia coli* expression system.

12. A method according to claim 7, wherein the biological material is a fusion protein comprising sequences of humam papillomavirus proteins (HPV).

13. A method according to claim 12, wherein the human papillomavirus porteins are from HPV L2 fused with E6, E7 or a combination of E6 and E7.

* * * * *